(12) United States Patent
Tang et al.

(10) Patent No.: US 11,461,899 B1
(45) Date of Patent: Oct. 4, 2022

(54) METHOD FOR DETECTING INFECTION STAGE OF ANTHRACNOSE PATHOGENIC WITH PRE-ANALYSIS CAPACITY

(71) Applicant: Guangdong Polytechnic Normal University, Guangzhou (CN)

(72) Inventors: Yu Tang, Guangzhou (CN); Shaoming Luo, Guangzhou (CN); Jiepeng Yang, Guangzhou (CN); Yiqing Fu, Guangzhou (CN); Jinfei Zhao, Guangzhou (CN); Jiahao Li, Guangzhou (CN); Zhiping Tan, Guangzhou (CN); Huasheng Huang, Guangzhou (CN); Qiwei Guo, Guangzhou (CN); Weizhao Chen, Guangzhou (CN)

(73) Assignee: GUANGDONG POLYTECHNIC NORMAL UNIVERSITY, Guangzhou (CN)

( * ) Notice: Subject to any disclaimer, the term of this patent is extended or adjusted under 35 U.S.C. 154(b) by 0 days.

(21) Appl. No.: 17/720,792

(22) Filed: Apr. 14, 2022

Related U.S. Application Data (63) Continuation of application No. 17/710,918, filed on Mar. 31, 2022.

(30) Foreign Application Priority Data

Oct. 29, 2021 (CN) .......................... 202111268572.4

(51) Int. Cl.
*G06K 9/00* (2022.01)
*G06T 7/00* (2017.01)
(Continued)

(52) U.S. Cl.
CPC ........... *G06T 7/0014* (2013.01); *G01N 21/65* (2013.01); *G01N 33/0098* (2013.01); *G06N 3/08* (2013.01);
(Continued)

(58) Field of Classification Search
CPC ......... G06T 7/0014; G06T 2207/20081; G06T 2207/20084; G06T 2207/20212;
(Continued)

(56) References Cited

U.S. PATENT DOCUMENTS

2014/0234438 A1 * 8/2014 De Seixas Boavida Ferreira ....... A01G 7/00 378/21

FOREIGN PATENT DOCUMENTS

| CA | 2969282 C * | 7/2018 | ............. A01N 25/00 |
| CN | 111246729 A * | 6/2020 | ............. F24F 11/49 |
| WO | WO-2021141896 A1 * | 7/2021 | |

* cited by examiner

*Primary Examiner* — Xin Jia
(74) *Attorney, Agent, or Firm* — Getech Law LLC; Jun Ye

(57) ABSTRACT

Disclosed is a method for detecting an infection stage of anthracnose pathogen with pre-analysis capacity, comprising: obtaining a plurality of sample sensing data sequences; obtaining a sample citrus leaf image; obtaining a first prediction result; if the first prediction result is that the sample citrus crop is not infected by anthracnose, obtaining sample Raman spectral data and sample hyperspectral data; obtaining a first judgment result, and obtaining a second judgment result; performing labeling to obtain second training data; training a neural network model to obtain a second anthracnose prediction model; obtaining a plurality of to-be-analyzed sensing data sequences; obtaining a to-be-analyzed citrus leaf image; obtaining a second prediction result; if the second prediction result is that the to-be-analyzed citrus crop (Continued)

is not infected by anthracnose, obtaining a third prediction result.

6 Claims, 2 Drawing Sheets

(51) Int. Cl.
*G06N 3/08* (2006.01)
*G06V 10/774* (2022.01)
*G06V 10/82* (2022.01)
*G06V 10/776* (2022.01)
*G01N 33/00* (2006.01)
*G01N 21/65* (2006.01)

(52) U.S. Cl.
CPC .......... *G06V 10/774* (2022.01); *G06V 10/776* (2022.01); *G06V 10/82* (2022.01); *G06T 2207/20081* (2013.01); *G06T 2207/20084* (2013.01); *G06T 2207/20212* (2013.01); *G06T 2207/30188* (2013.01)

(58) Field of Classification Search
CPC .......... G06T 2207/30188; G01N 21/65; G01N 33/0098; G06N 3/08; G06V 10/774; G06V 10/776; G06V 10/82
See application file for complete search history.

METHOD FOR DETECTING INFECTION STAGE OF ANTHRACNOSE PATHOGENIC WITH PRE-ANALYSIS CAPACITY

CROSS-REFERENCE TO RELATED APPLICATION

This application is a continuation of U.S. patent application Ser. No. 17/710,918, filed Mar. 31, 2022, the content of which application is hereby expressly incorporated herein by reference in its entirety.

TECHNICAL FIELD

The present application relates to the field of smart agriculture, and in particular relates to a method for detecting an infection stage of anthracnose pathogen with pre-analysis capacity.

BACKGROUND

Citrus anthracnose is a frequently-occurring disease in various citrus producing areas in China, especially in seasons with low air temperature and more cloudy and rainy days. Citrus crops are susceptible to anthracnose pathogen (a fungus, mainly *C. gloeosporioides*), which often leads to massive leaf drop, fruit drop, branch tip dieback and bark burst of the infected crops, and may lead to the die of the whole plant in severe cases, while the diseased fruits are also prone to rotting during storage and transportation, which seriously threatens the entire citrus industry. Therefore, research on the monitoring and control methods of citrus anthracnose, especially the early detection and diagnosis of the disease, can effectively improve the accuracy of the application prescription decision and the target of integrated control, which is conducive to avoiding disease attacks and spread over a large area.

According to the period of infection and symptom appearance of fungal diseases of crops, the infection progress can be approximately divided into three main stages: a pathogen penetration period, an incubation period, and symptom appearance. The pathogen penetration period is a period of time that the pathogen penetrates into the crops and establishes a parasitic relationship with the crops; the incubation period is the period when the pathogen absorbs nutrition in the crop, grows and spreads to cause damage from the establishment of the parasitic relationship to the time before symptom appearance of the disease; the symptom appearance refers to a period of time after symptom appearance of the disease, disease spots at the moment can be generally diagnosed by experts and observed by naked eyes, the diseases in this period have the ability to diffuse and spread from points to faces and cause the damage over a large area, and the hysteresis of disease diagnosis (for example, diagnosis is conducted in symptom appearance) is an important reason for large-area spread of the diseases.

Therefore, if the rapid detection and diagnosis of the disease can be conducted prior to the symptom appearance, it is beneficial to control the disease, conduct targeted drug control and stop the spread of the disease over a large area.

SUMMARY

A method for detecting an infection stage of anthracnose pathogen with pre-analysis capacity is provided, comprising the following steps:

S1: performing data acquisition processing in a first time cycle using a plurality of sensors arranged in a sample area, thus obtaining a plurality of sample sensing data sequences, wherein the plurality of sample sensing data sequences at least comprise a temperature data sequence and a humidity data sequence, sample citrus crops are planted in the sample area, and the sample citrus crops have not been found to be infected by the anthracnose pathogen prior to the first time cycle;

S2: performing image acquisition processing on a leaf of the sample citrus crop using a preset camera to obtain a sample citrus leaf image;

S3: inputting the sample citrus leaf image into a preset first anthracnose prediction model for processing to obtain a first prediction result output by the first anthracnose prediction model, and judging whether the first prediction result is that the sample citrus crop is infected by anthracnose, wherein the first anthracnose prediction model is obtained by training by taking a leaf image of the citrus crop in symptom appearance as first training data based on a deep convolutional neural network model; and the infection progress of the anthracnose pathogen to the citrus crop is totally divided into three stages: a penetration period, an incubation period, and symptom appearance;

S4: if the first prediction result is that the sample citrus crop is not infected by anthracnose, performing Raman spectral detection and hyperspectral detection on the leaf of the sample citrus crop respectively to obtain sample Raman spectral data and sample hyperspectral data;

S5: judging whether the leaf of the sample citrus crop is in the penetration period or not according to the sample Raman spectral data, thus obtaining a first judgment result; and judging whether the leaf of the sample citrus crop is in the incubation period or not according to the sample hyperspectral data, thus obtaining a second judgment result;

S6, performing labeling on the plurality of sample sensing data sequences to label the first judgment result and the second judgment result, thus obtaining second training data;

S7, training a preset neural network model using the second training data to obtain a second anthracnose prediction model;

S8, performing data acquisition processing in a second time cycle using a plurality of sensors arranged in a to-be-analyzed area, thus obtaining a plurality of to-be-analyzed sensing data sequences, wherein the types of the plurality of to-be-analyzed sensing data sequences are the same as the types of the plurality of sample sensing data sequences in a one-to-one correspondence manner, to-be-analyzed citrus crops are planted in the to-be-analyzed area, and the to-be-analyzed citrus crops have not been found to be infected by the anthracnose pathogen prior to the second time cycle;

S9, performing image acquisition processing on a leaf of the to-be-analyzed citrus crop using a preset camera to obtain a to-be-analyzed citrus leaf image;

S10, inputting the to-be-analyzed citrus leaf image into the first anthracnose prediction model for processing to obtain a second prediction result output by the first anthracnose prediction model, and judging whether the second prediction result is that the to-be-analyzed citrus crop is infected by anthracnose;

S11, if the second prediction result is that the to-be-analyzed citrus crop is not infected by anthracnose, inputting the plurality of to-be-analyzed sensing data sequences into the second anthracnose prediction model for processing to obtain a third prediction result, wherein the third prediction result is that the leaf of the to-be-analyzed citrus crop is in the penetration period, in the incubation period, or is not infected by the anthracnose pathogen;

S12, if the third prediction result is that the leaf of the to-be-analyzed citrus crop is in the penetration period, generating a Raman spectral detection instruction to indicate to perform Raman spectral detection processing on the to-be-analyzed citrus crop; and S13, if the third prediction result is that the leaf of the to-be-analyzed citrus crop is in the incubation period, generating a hyperspectral detection instruction to indicate to perform hyperspectral detection on the to-be-analyzed citrus crop.

Further, prior to the step S3 of inputting the sample citrus leaf image into a preset first anthracnose prediction model for processing to obtain a first prediction result output by the first anthracnose prediction model and judging whether the first prediction result is that the sample citrus crop is infected by anthracnose, the method comprises:

S21, retrieving a plurality of sample images from a preset database, wherein the sample images are images obtained by collecting leaves of a citrus crop in symptom appearance;

S22, dividing the plurality of sample images into a plurality of training images and a plurality of verifying images according to a preset proportion;

S23, retrieving a preset deep convolutional neural network model, and inputting the plurality of training images into the deep convolutional neural network model for training to obtain a temporary anthracnose prediction model;

S24, performing verification processing on the temporary anthracnose prediction model using the plurality of verifying images, and judging whether a verification processing result is that the verification is passed; and S25, if the verification processing result is that the verification is passed, recording the temporary anthracnose prediction model as the first anthracnose prediction model.

Further, the step S21 of retrieving a plurality of sample images from a preset database, wherein the sample images are images obtained by collecting leaves of the citrus crop in the symptom appearance, comprises:

S211, performing image acquisition processing on the front and the back of one leaf of the citrus crop in the symptom appearance to obtain a front image and a back image; and S212, combining the front image and the back image corresponding to each other into a common image, and recording the common image as a sample image.

Further, the step S9 of performing image acquisition processing on a leaf of the to-be-analyzed citrus crop using a preset camera to obtain a to-be-analyzed citrus leaf image comprises:

S901, performing data acquisition processing on the fronts and the backs of a plurality of leaves of the to-be-analyzed citrus crop using the preset camera to obtain a plurality of front images and a plurality of back images;

S902, combining the front image and the back image obtained by performing the image acquisition on the same leaf into a combined image, thus obtaining a plurality of combined images, correspondingly; and S903, generating a combined image processing instruction to indicate to sequentially input the plurality of combined images into the first anthracnose prediction model for processing.

Further, after the step S10 of inputting the to-be-analyzed citrus leaf image into the first anthracnose prediction model for processing to obtain a second prediction result output by the first anthracnose prediction model, and judging whether the second prediction result is that the to-be-analyzed citrus crop is infected by anthracnose, the method comprises:

S101, if the second prediction result is that the to-be-analyzed citrus crop is infected by anthracnose, retrieving a plurality of sensing data sequences for a designated area;

S102, calculating a similarity value between the plurality of sensing data sequences for the designated area and the plurality of to-be-analyzed sensing data sequences according to a preset similarity calculation method;

S103, judging whether the similarity value is greater than a preset similarity threshold or not; and S104, if the similarity value is greater than the preset similarity threshold, generating an early detection instruction to indicate to input the plurality of sensing data sequences for the designated area into the first anthracnose prediction model for processing after completing the detection of the to-be-analyzed sensing data sequences.

A means for detecting an infection stage of anthracnose pathogen with pre-analysis capacity is provided, comprising:

a sample sensing data sequence acquisition unit for indicating to perform data acquisition processing in a first time cycle using a plurality of sensors arranged at a sample area, thus obtaining a plurality of sample sensing data sequences, wherein the plurality of sample sensing data sequences at least comprise a temperature data sequence and a humidity data sequence, sample citrus crops are planted in the sample area, and the sample citrus crops have not been found to be infected by the anthracnose pathogen prior to the first time cycle;

a sample citrus leaf image acquisition unit for indicating to perform image acquisition processing on a leaf of the sample citrus crop using a preset camera to obtain a sample citrus leaf image;

a first prediction result judgment unit for indicating to input the sample citrus leaf image into the first anthracnose prediction model for processing to obtain a first prediction result output by the first anthracnose prediction model, and judging whether the first prediction result is that the sample citrus crop is infected by anthracnose, wherein the first anthracnose prediction model is obtained by training by taking a leaf image of a citrus crop in symptom appearance as first training data based on a deep convolutional neural network model; and the infection progress of the anthracnose pathogen to the citrus crop is totally divided into three stages: a penetration period, an incubation period, and symptom appearance;

a sample Raman spectral data acquisition unit for indicating to perform Raman spectral detection and hyperspectral detection processing on the leaf of the sample citrus crop respectively if the first prediction result is that the sample citrus crop is not infected by anthracnose, thus obtaining sample Raman spectral data and sample hyperspectral data;

a first judgment result acquisition unit for indicating to judge whether the leaf of the citrus crop is in the penetration period or not according to the sample Raman spectral data, thus obtaining a first judgment result, and indicating to judge whether the leaf of the sample citrus crop is in the incubation period or not according to the sample hyperspectral data, thus obtaining a second judgment result;

a second training data acquisition unit for indicating to perform labeling on the plurality of sample sensing data sequences to label the first judgment result and the second judgment result, thus obtaining second training data;

a second anthracnose prediction model acquisition unit for indicating to perform training on the preset neural network model using the second training data to obtain a second anthracnose prediction model;

a to-be-analyzed sensing data sequence acquisition unit for indicating to perform data acquisition processing in a second time cycle using a plurality of sensors arranged in a to-be-analyzed area, thus obtaining a plurality of to-be-analyzed sensing data sequences, wherein the types of the plurality of to-be-analyzed sensing data sequences are the same as the types of the plurality of sample sensing data sequences in a one-to-one correspondence manner, to-be-analyzed citrus crops are planted in the to-be-analyzed area, and the to-be-analyzed citrus crops have not been found to be infected by the anthracnose pathogen prior to the second time cycle;

a to-be-analyzed citrus leaf image acquisition unit for indicating to perform image acquisition processing on a leaf of a to-be-analyzed citrus crop using a preset camera to obtain a to-be-analyzed citrus leaf image;

a second prediction result judgment unit for indicating to input the to-be-analyzed citrus leaf image into the first anthracnose prediction module for processing to obtain a second prediction result output by the first anthracnose prediction model, and judging whether the second prediction result is that the to-be-analyzed citrus crop is infected by anthracnose;

a third prediction result acquisition unit for indicating to input the plurality of to-be-analyzed sensing data sequences into the second anthracnose prediction model for processing if the second prediction result is that the to-be-analyzed citrus crop is not infected by anthracnose, thus obtaining a third prediction result, wherein the third prediction result is that the leaf of the to-be-analyzed citrus crop is in the penetration period, in the incubation period or is not infected by the anthracnose pathogen;

a Raman spectral detection instruction generation unit for indicating to generate a Raman spectral detection instruction if the third prediction result is that the leaf of the to-be-analyzed citrus crop is in the penetration period, thus indicating to perform Raman spectral detection processing on the to-be-analyzed citrus crop; and a hyperspectral detection instruction generation unit for indicating to generate a hyperspectral detection instruction if the third detection result is that the leaf of the to-be-analyzed citrus crop is in the incubation period, thus indicating to perform hyperspectral detection processing on the to-be-analyzed citrus crop.

A computer apparatus is provided by the present application, comprising a memory and a processor, the memory stores computer programs, and the processor implements the steps of the method of any one of above when executing the computer programs.

A computer readable storage medium having computer programs stored thereon is provided by the present application, the computer programs, when executed by a processor, implement the steps of the method of any one of above.

A method and means for detecting an infection stage of anthracnose pathogen with pre-analysis capacity, a computer apparatus and a storage medium are provided. The method comprises: obtaining a plurality of sample sensing data sequences; obtaining a sample citrus leaf image; obtaining a first prediction result output by a first anthracnose prediction model; if the first prediction result is that a sample citrus crop is not infected by anthracnose, obtaining sample Raman spectral data and sample hyperspectral data; obtaining a first judgment result, and obtaining a second judgment result; performing labeling on the plurality of sample sensing data sequences to label the first judgment result and the second judgment result, thus obtaining second training data; training a neural network model to obtain a second anthracnose prediction model; obtaining a plurality of to-be-analyzed sensing data sequences; obtaining a to-be-analyzed citrus leaf image; obtaining a second prediction result output by the first anthracnose prediction model; if the second prediction result is that a to-be-analyzed citrus crop is not infected by anthracnose, obtaining a third prediction result; if the third prediction result is that a leaf of the to-be-analyzed citrus crop is in the penetration period, generating a Raman spectral detection instruction; if the third prediction result is that the leaf of the to-be-analyzed citrus crop is in the incubation period, generating a hyperspectral detection instruction, thus completing the pre-analysis to the infection progress of the anthracnose pathogen, and achieving rapid detection prior to the symptom appearance of anthracnose.

Wherein the pre-analysis in the present application refers to pre-analysis of which detection mode should be adopted for the citrus in the to-be-analyzed area, i.e., whether the Raman spectral detection or hyperspectral detection, while the two detection modes are respectively suitable for detecting the two stages of the penetration period and the incubation period of the pathogen.

Wherein if the scheme for detecting the infection stage of the anthracnose pathogen with pre-analysis capacity of the present application is not adopted, as the disease spots in the symptom appearance can generally be diagnosed by experts and observed by the naked eyes, the diagnosis for the citrus crop in the symptom appearance at the to-be-analyzed area is easy. If the citrus crop is in the two periods of the penetration period and the incubation period of the pathogen, due to the fact that it is impossible to judge which stage the citrus crop may be in, the detection processing of the two stages needs to be conducted simultaneously, for example, the Raman spectral detection and the hyperspectral detection need to be conducted simultaneously, which may lead to repeated detection, resulting in the situations of the waste of detection resources and the increase of the cost.

Hence, due to the pre-analysis capacity of the detection of the infection stage of the anthracnose pathogen with the pre-analysis capacity, whether the Raman spectral detection or hyperspectral detection should be used can be previously analyzed (certainly, just in case and for data integrity, one detection can be followed by another detection, e.g. Raman spectral detection can be followed by hyperspectral detection). However, in any case, preferential detection processing should be conducted according to a detection mode corresponding to an instruction given by the pre-analysis, while the other detection can be deferred absolutely. Therefore, in this case, the scheme of the present application still has the advantages of time and efficiency, thus allowing earlier and more targeted detection to determine whether the anthracnose pathogen exists or not and to determine a specific infection stage.

Achievement, functional features and advantages of the objectives of the present application will be further described with reference to the accompanying drawings and in conjunction with the embodiments.

DETAILED DESCRIPTION OF EMBODIMENTS

To make the objectives, technical solutions and advantages of the present application more clearly, the present application is further described in detail with conjunction with the accompanying drawings and the embodiments. It should be understood that specific embodiments described here are merely illustrative of the present application and are not intended to limit the present application.

Figure 1:
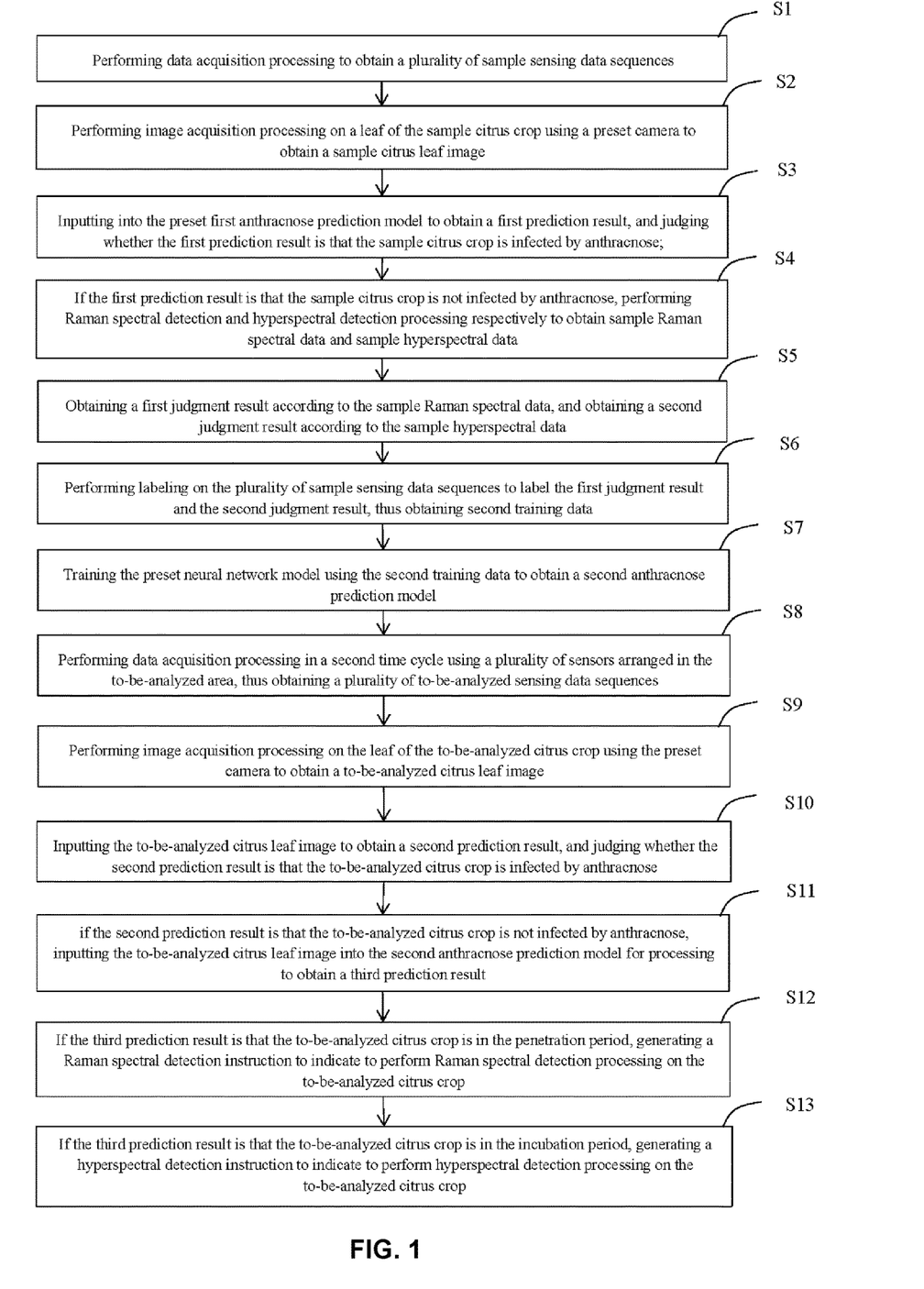
FIG. 1 is a process diagram of a method for detecting an infection stage of anthracnose pathogen with pre-analysis capacity of one embodiment of the present application.

Referring to FIG. 1, a method for detecting an infection stage of anthracnose pathogen with pre-analysis capacity is provided by an embodiment of the present application, comprising the following steps:

S1: performing data acquisition processing in a first time cycle using a plurality of sensors arranged in a sample area, thus obtaining a plurality of sample sensing data sequences, wherein the plurality of sample sensing data sequences at least comprise a temperature data sequence and a humidity data sequence, sample citrus crops are planted in the sample area, and the sample citrus crops have not been found to be infected by the anthracnose pathogen prior to the first time cycle;

S2: performing image acquisition processing on a leaf of the sample citrus crop using a preset camera to obtain a sample citrus leaf image;

S3: inputting the sample citrus leaf image into a preset first anthracnose prediction model for processing to obtain a first prediction result output by the first anthracnose prediction model, and judging whether the first prediction result is that the sample citrus crop is infected by anthracnose, wherein the first anthracnose prediction model is obtained by training by taking a leaf image of the citrus crop in symptom appearance as first training data based on a deep convolutional neural network model; and the infection progress of the anthracnose pathogen to the citrus crop is totally divided into three stages: a penetration period, an incubation period, and symptom appearance;

S4: if the first prediction result is that the sample citrus crop is not infected by anthracnose, performing Raman spectral detection and hyperspectral detection on the leaf of the sample citrus crop respectively to obtain sample Raman spectral data and sample hyperspectral data;

S5: judging whether the leaf of the sample citrus crop is in the penetration period or not according to the sample Raman spectral data, thus obtaining a first judgment result; and judging whether the leaf of the sample citrus crop is in the incubation period or not according to the sample hyperspectral data, thus obtaining a second judgment result;

S6, performing labeling on the plurality of sample sensing data sequences to label the first judgment result and the second judgment result, thus obtaining second training data;

S7, training a preset neural network model using the second training data to obtain a second anthracnose prediction model;

S8, performing data acquisition processing in a second time cycle using a plurality of sensors arranged in a to-be-analyzed area, thus obtaining a plurality of to-be-analyzed sensing data sequences, wherein the types of the plurality of to-be-analyzed sensing data sequences are the same as the types of the plurality of sample sensing data sequences in a one-to-one correspondence manner, to-be-analyzed citrus crops are planted in the to-be-analyzed area, and the to-be-analyzed citrus crops have not been found to be infected by the anthracnose pathogen prior to the second time cycle;

S9, performing image acquisition processing on a leaf of the to-be-analyzed citrus crop using a preset camera to obtain a to-be-analyzed citrus leaf image;

S10, inputting the to-be-analyzed citrus leaf image into the first anthracnose prediction model for processing to obtain a second prediction result output by the first anthracnose prediction model, and judging whether the second prediction result is that the to-be-analyzed citrus crop is infected by anthracnose;

S11, if the second prediction result is that the to-be-analyzed citrus crop is not infected by anthracnose, inputting the plurality of to-be-analyzed sensing data sequences into the second anthracnose prediction model for processing to obtain a third prediction result, wherein the third prediction result is that the leaf of the to-be-analyzed citrus crop is in the penetration period, in the incubation period, or is not infected by the anthracnose pathogen;

S12, if the third prediction result is that the leaf of the to-be-analyzed citrus crop is in the penetration period, generating a Raman spectral detection instruction to indicate to perform Raman spectral detection processing on the to-be-analyzed citrus crop; and S13, if the third prediction result is that the leaf of the to-be-analyzed citrus crop is in the incubation period, generating a hyperspectral detection instruction to indicate to perform hyperspectral detection on the to-be-analyzed citrus crop.

As described in the steps S1-S5, the plurality of sensors are arranged at the sample area to perform data acquisition processing in the first time cycle, thus obtaining the plurality of sample sensing data sequences, wherein the plurality of sample sensing data sequences at least comprise the temperature data sequence and the humidity data sequence, sample citrus crops are planted in the sample area, and the sample citrus crops have not been found to be infected by the anthracnose pathogen prior to the first time cycle; and the preset camera is used to perform image acquisition processing on the leaf of the sample citrus crop to obtain the sample citrus leaf image;

The sample citrus leaf image is input into the preset first anthracnose prediction model for processing to obtain a first prediction result output by the first anthracnose prediction model, and whether the first prediction result is that the sample citrus crop is infected by anthracnose is judged, wherein the first anthracnose prediction model is obtained by taking a leaf image of the citrus crop in symptom appearance as first training data based on a deep convolutional neural network model; and the infection progress of the anthracnose pathogen to the citrus crop is totally divided into three stages: a penetration period, an incubation period, and symptom appearance. If the first prediction result is that the sample citrus crop is not infected by anthracnose, the Raman spectral detection processing and the hyperspectral spectral detection processing are conducted on the leaf of the sample citrus crop respectively to obtain the sample Raman spectral data and the sample hyperspectral data; and whether the leaf of the sample citrus crop is in the penetration period is judged according to the sample Raman spectral data to obtain the first judgment result, and whether the leaf of the sample citrus crop is in the incubation period is judged according to the sample hyperspectral data to obtain the second judgment result.

The implementation concept of the present application is that: assuming that no anthracnose pathogen exists in a certain area, there is no difference between implementing the scheme of the present application and implementing other schemes of the prior art; and assuming that the anthracnose pathogen exists in a certain area, the implementation of the scheme of the present application can determine an infection stage of anthracnose pathogen earlier, and more accurate and targeted.

Therefore, it is assumed that the anthracnose pathogen exists in a certain area, while the anthracnose pathogen can grow in an appropriate environment and is difficult to grow in an inappropriate environment, the optimal growth environment of which is the temperature of approximate 28° C. and relative humidity of 75% (certainly, other environmental parameters may affect the growth of the anthracnose pathogen). Therefore, the environmental parameters can reflect the growth speed of the anthracnose pathogen, provided that the anthracnose pathogen exists in this area, that is the reason for setting of assumption in the present application (certainly, if no anthracnose pathogen exists in this area in fact, there will be no disease, the final result obtained by employing any conventional detection mode, such as directly employing the Raman spectral detection, is the same as that of the present application, and thus no loss is caused). Therefore, the infection stage of the anthracnose pathogen to the citrus crop can be predicted as sufficient sensing data are acquired. The sensing data may also include air pressure values, soil composition values, growth conditions of citrus crops, and other relevant parameters. In conclusion, the more the sensing data, the better the implementation of the present application. However, in any case, the data must include at least temperature and humidity.

Moreover, the sample area has another feature, i.e., the sample citrus crops have not been found to be infected by the anthracnose pathogen prior to the first time cycle. Therefore, the data acquisition in the sample area is conducted periodically. The reason for such processing is to guarantee that the citrus crops corresponding to the sample sensing data sequences are not infected by the anthracnose pathogen previously as much as possible, because the citrus crops which have been infected previously are not conducive to the implementation of the present application (which may introduce additional influence factors). Each sequence in the plurality of sample sensing data sequences is the time sequence.

Then the sample citrus leaf image is acquired and input into the preset first anthracnose prediction model for processing to obtain the first prediction result output by the first anthracnose prediction model, and whether the first prediction result is that the sample citrus crop is infected by anthracnose is judged. As the citrus leaf in the symptom appearance is prone to spotting, the citrus leaf infected by anthracnose is easy to be detected. Accordingly, whether the sample citrus crop is infected by anthracnose is judged by using the first anthracnose prediction model obtained by training based on the deep convolutional neural network model. The first anthracnose prediction model is a picture processing model, which is therefore obtained by adopting the deep convolutional neural network model suitable for image classification and other processing as a prototype, and taking the leaf image of the citrus crop in symptom appearance as the first training data on this basis. Wherein a back propagation algorithm can be adopted in the training process to update parameters of each network.

It needs to be noted that the first anthracnose prediction model can only be used to judge whether the citrus crop is in the symptom appearance, but not for the other two infection stages.

If the first prediction result is that the sample citrus crop is not infected by anthracnose, the Raman spectral detection processing and the hyperspectral detection processing are respectively conducted on the leaf of the sample citrus crop to obtain the sample Raman spectral data and the sample hyperspectral data. Wherein the sample Raman spectral data and the sample hyperspectral data are respectively used for judging whether the crop is in the penetration period and the incubation period or not.

The reason why the sample Raman spectral data can be used to judge whether the crop is in the penetration period is that after penetration of the pathogen, cell walls of the citrus leaf are damaged and polysaccharide and other substances in the cell walls are changed, and the Raman spectra can better observe these changes, thus achieving the detection of the penetration period of the anthracnose.

The specific process is approximately as follows:

embedding a sample, and performing electron microscope and surface-enhanced Raman sample preparation; debugging parameters of a Raman spectral acquisition system, selecting a laser source with an appropriate wavelength, acquiring Raman spectral data information of a citrus leaf sample, and improving a Raman spectral signal-to-noise ratio through a spectral preprocessing method;

after spectral acquisition, observing a cell microstructure of a leaf inoculation area using a scanning electron microscope, and detecting chemical parameter values such as cell wall polysaccharide, anti-peroxidase and intracellular pH by using instruments such as liquid chromatography and a pH detector to serve as a basis for spectral data analysis;

achieving data dimension conversion using principal component analysis, processing the confocal microscopic Raman spectrum of the cell wall using K-means clustering or set coverage and other clustering algorithms, thus achieving spatial qualitative division of the cell wall in a micron level; determining a spectral band with obvious wave crests and excellent specificity as a quantitative peak (which can be screened by means of a computer optimization algorithm and a chemometrics method), and establishing a quantitative calibration curve by means of a standard substance, thus achieving quantitative detection of components such as cell wall polysaccharide, anti-peroxidase and intracellular pH;

and in combination with a cell wall microscopic image and a Raman spectrum fingerprint band, drawing a spatial distribution map of each component in the cell according to Raman fingerprint band information of polysaccharide components, pH and the like, thus achieving the positioning detection of the cell wall polysaccharide of the citrus leaf; and then comparing the positioning detection data with standard data to learn whether the citrus crop is in the penetration period of the citrus anthracnose pathogen.

As the present application mainly relates to pre-analysis, the process of the Raman spectral detection is not extended in detail.

Similarly, the reason why the sample hyperspectral data can be used to judge whether the crop is in the incubation period is that the incubation period is closely related to the change of indexes such as antioxidant enzyme of the citrus leaf, so that whether the crop is in the incubation period of the anthracnose can be diagnosed by detecting the indexes such as antioxidant enzyme.

The specific process is approximately as follows:

selecting a sample leaf, and taking a normally growing leaf as a reference sample;

adjusting parameters of a hyperspectral acquisition system, acquiring hyperspectral data, and improving a spectral signal-to-noise ratio using a spectral preprocessing method;

after spectral acquisition, detecting antioxidant enzyme activity and chlorophyll, water content and like at different positions of the sample using high-precision pathological detection methods such as ELISA (Enzyme-Linked Immuno Sorbent Assay), PCR (Polymerase Chain Reaction), water activity meter and like, which are used as references for spectral analysis.

researching dynamic response rules and quantitative change models of the antioxidant enzyme activity, the chlorophyll, moisture and infection time and degree of the citrus leaf in normal and pathological states respectively after being infected by the anthracnose gloeosporioides by utilizing a chemometrics method such as characteristic wavelength extraction, image characteristic extraction and linear and nonlinear modeling methods, and establishing a quantitative relationship model of *Colletotrichum gloeosporioides* infection in the incubation period; and drawing a corresponding spatial distribution map in the leaf to achieve dynamic monitoring of the content and distribution of the chemical components in the incubation period of the citrus anthracnose, and then establishing a rapid detection model for in-vivo detection, dynamic detection and batch samples of physiological and pathological information of the citrus fruit/leaf under the stress of the *Colletotrichum gloeosporioides*, thus determining whether the citrus crop is in the incubation period of the anthracnose pathogen.

Similarly, as the present application mainly relates to pre-analysis, the process of the hyperspectral detection is not extended in detail.

Wherein hyper-spectrum is a proprietary term, which is defined as a three-dimensional "atlas-in-one" image formed by the combination of imaging and spectral technologies, including two-dimensional spatial information and one-dimensional spectral information, and containing tens to hundreds of continuous resolution, narrow-band image data, which record the electromagnetic wave signal or energy of a feature and can be used to create a mathematical model to describe the characteristics of the feature.

Accordingly, the first judgment result and the second judgment result can be obtained. Wherein the first judgment result and the second judgment result are actually used for labeling, which is also a feature of the present application. In the process of steps S1-S5, the purpose is to determine the training data. The main reason why no previous models have been able to perform pre-analysis is the lack of training data. The sensing data sequence has an implicit association with what infection stage the citrus crop is in (at the moment, pathogen exists by default), for example, when the environment represented by the sensing data sequence is suitable for rapid growth of the anthracnose pathogen, the citrus is more likely to be in the incubation period (as the precondition is that the citrus has not entered symptom appearance, and has not been infected by anthracnose prior to the detection of the first cycle, which is also a reason for periodic detection). Certainly, it is also related to the time length corresponding to the sensing data sequence; and when the environment represented by the sensing data sequence is not suitable for the growth of anthracnose pathogen, the citrus is more likely to be in the penetration period. Certainly, when the environment represented by the sensing data sequence is highly unfavorable for the growth of the anthracnose pathogen, the citrus crop is not susceptible to anthracnose.

For such association, different sample sensing data sequences may correspond to different infection stages through the steps S1-S5 in the present application, so that the establishment of a pre-analysis model becomes possible.

As described in steps S6-S10 above, the plurality of sample sensing data sequences are labeled to label out the first judgment result and the second judgment result, thus obtaining the second training data; the second training data is used to train the preset neural network model to obtain the second anthracnose prediction model; a plurality of sensors arranged at the to-be-analyzed area are used to perform data acquisition processing in the second time cycle, thus obtaining a plurality of to-be-analyzed sensing sequences, wherein the types of the plurality of to-be-analyzed sensing data sequences are in one-to-one correspondence with the types of the plurality of sample sensing data sequences, to-be-analyzed citrus crops are planted in the to-be-analyzed area, and the to-be-analyzed citrus crops have not been found to be infected by the anthracnose pathogen prior to the second time cycle; the preset camera is used to perform image acquisition processing on the leaf of the to-be-analyzed citrus crop to obtain the to-be-analyzed citrus leaf image, and the to-be-analyzed citrus crop leaf image is input into the first anthracnose prediction model for processing to obtain the second prediction result output by the first anthracnose prediction model, and whether the second prediction result is that the to-be-analyzed citrus crop is infected by the anthracnose is judged.

The first judgment result and the second judgment result respectively indicate whether the to-be-analyzed citrus crop is in the penetration stage or in the incubation stage. Wherein when the first judgment result and the second judgment result are both that the to-be-analyzed citrus crop is infected by anthracnose, it is labeled as the incubation stage; if the first judgment result is that the to-be-analyzed citrus crop is not infected by anthracnose and the second judgment result is that the to-be-analyzed citrus crop is infected by anthracnose, it is labeled as the incubation stage; if the first judgment result is that the to-be-analyzed citrus crop is infected by anthracnose and the second judgment result is that the to-be-analyzed citrus crop is not infected by anthracnose, it is labeled as the penetration stage; and if the first judgment result is that the to-be-analyzed citrus crop is not infected by anthracnose and the second judgment result is that the to-be-analyzed citrus crop is not infected by anthracnose, it is labeled as no disease.

The neural network model in the present application can specifically be any feasible model, such as a long short-term memory network model, an adversarial network model, a residual network model and the like. The present application does not employ any specific design in the structure of the neural network model, thus any existing feasible model can be employed. For example, a training mode with supervised learning (because labeled sample data are adopted) can be adopted, and a back propagation model can be adopted for network parameter updating.

The plurality of sensors arranged at the to-be-analyzed area are then used to perform data acquisition processing in the second time cycle, thus obtaining the plurality of to-be-analyzed sensing data sequences. The plurality of to-be-analyzed sensing data sequence are in one-to-one correspondence with the plurality of sample sensing data sequences above, thus the employed sensors are in one-to-one correspondence. Similarly, as the citrus crops in the area corresponding to the plurality of sample sensing data sequences have not been found to be infected by the anthracnose pathogen prior to the first time cycle, the to-be-analyzed citrus crops are planted in the to-be-analyzed area in the present application, and the to-be-analyzed citrus crops have not been found to be infected by the anthracnose pathogen prior to the second time cycle.

The preset camera is then used to perform image acquisition processing on the leaf of the to-be-analyzed citrus crop to obtain the to-be-analyzed citrus leaf image, and then the second prediction result can be obtained by using the first anthracnose prediction model. Wherein the processing of the first anthracnose prediction model to the to-be-analyzed citrus leaf image is the same as the processing of the first anthracnose prediction model to the sample citrus leaf image. The processing at the moment is to determine whether the to-be-analyzed citrus is in obvious symptom appearance or not. If the to-be-analyzed citrus is in the symptom appearance, the symptoms may appear clearly on the leaf, thus no subsequent steps are required. If the to-be-analyzed citrus is not in the symptom appearance, the pre-analysis processing can be continued.

As described in steps S11-S13, if the second prediction result is that the to-be-analyzed citrus crop is not infected by anthracnose, the plurality of to-be-analyzed sensing data sequences are input into the second anthracnose prediction model for processing to obtain the third prediction result, wherein the third prediction result is that the to-be-analyzed citrus crop is in the penetration period, in the incubation period, or not infected by the anthracnose pathogen; if the third prediction result is that the to-be-analyzed citrus crop is in the penetration period, the Raman spectral detection instruction is generated to indicate to perform Raman spectral detection processing on the to-be-analyzed citrus crop; if the third prediction result is that the to-be-analyzed citrus crop is in the incubation period, the hyperspectral detection instruction is generated to indicate to perform hyperspectral detection processing on the to-be-analyzed citrus crop.

if the second prediction result is that the to-be-analyzed citrus crop is not infected by anthracnose, it is indicated that the to-be-analyzed citrus is not in obvious symptom appearance, thus the third prediction result can be obtained by using the second anthracnose prediction model obtained through training. A corresponding detection instruction is then generated according to the third prediction result. That is, as the Raman spectrum is suitable for detecting the penetration period while the hyper-spectrum is suitable for detecting the incubation period, if the third prediction result is that the to-be-analyzed citrus crop is in the penetration period, the Raman spectral detection instruction is generated to indicate to perform Raman spectral detection processing on the to-be-analyzed citrus crop, and if the third prediction result is that the to-be-analyzed citrus crop is in the incubation period, the hyperspectral detection instruction is generated to indicate to perform hyperspectral detection processing on the to-be-analyzed citrus crop. Moreover, the specific Raman spectral detection process and the hyperspectral detection process are consistent with the detection of the leaf of the sample citrus crop.

In addition, in the present application, although the number of sample areas, or other, the number (namely the number of the plurality of sample sensing data sequences) of the plurality of sample sensing data sequences corresponding in batches as a whole is not mentioned, and the number of sample citrus leaf images is not mentioned, it can be known from the intrinsic characteristics of the machine learning that a plurality of training data are required in the training process, and therefore the number of the sample areas can be multiple. The number of the plurality of sample sensing data sequences corresponding in batches as a whole should be multiple and the number of the sample citrus leaf images should be multiple, which is a default in the art. Moreover, in order to prevent the introduction of a description of the number from making the introduction of the scheme unclear, the description of the number is not described in detail foregoing.

In one embodiment, prior to the step S3 of inputting the sample citrus leaf image into the preset first anthracnose prediction model for processing to obtain a first prediction result output by the first anthracnose prediction model, and judging whether the first prediction result is that the sample citrus crop is infected by anthracnose, the method comprises:

S21, retrieving a plurality of sample images from a preset database, wherein the sample images are images obtained by collecting leaves of a citrus crop in symptom appearance;

S22, dividing the plurality of sample images into a plurality of training images and a plurality of verifying images according to a preset proportion;

S23, retrieving a preset deep convolutional neural network model, and inputting the plurality of training images into the deep convolutional neural network model for training to obtain a temporary anthracnose prediction model;

S24, performing verification processing on the temporary anthracnose prediction model using the plurality of verifying images, and judging whether a verification processing result is that the verification is passed; and S25, if the verification processing result is that the verification is passed, recording the temporary anthracnose prediction model as the first anthracnose prediction model.

For the training of the first anthracnose prediction model in the present application, the used training data is an image obtained by acquiring a leaf of the citrus crop in the symptom appearance, thus a semi-supervised learning mode is employed for training. Due to the disease spots of the leaf of the citrus crop in the symptom appearance is apparent than that of a normal leaf, the image of the normal leaf cannot be used as a training object, i.e., compared with the training modes of other models, the training mode of the method provided by the present application may employ a semi-supervised learning mode for training, and the model obtained by training is not much different from a model obtained by employing a full-supervised learning mode. However, the training speed is improved as the number of training data is reduced to some extent. Then, as the training image and the verifying image are homologous and both are divided from the sample images, the first anthracnose prediction model obtained by training is able to perform the detection of whether the citrus crop enters the symptom appearance or not. Wherein the deep convolutional neural network model is obtained by connecting multi-layer network structures such as an input layer, a convolutional layer, a pooling layer, a fully connected layer and an output layer, some of which may have multiple layers.

Further, the step S21 of retrieving a plurality of sample images from a preset database, wherein the sample images are images obtained by collecting leaves of the citrus crop in the symptom appearance, comprises:

S211, performing image acquisition processing on the front and the back of one leaf of the citrus crop in the symptom appearance to obtain a front image and a back image; and S212, combining the front image and the back image corresponding to each other into a common image, and recording the common image as a sample image.

Therefore, the image acquisition is more accurate to reduce the possibility of misjudgment of the trained model.

Further, the step S9 of performing image acquisition processing on a leaf of the to-be-analyzed citrus crop using a preset camera to obtain a to-be-analyzed citrus leaf image comprises:

S901, performing data acquisition processing on the fronts and the backs of a plurality of leaves of the to-beanalyzed citrus crop using the preset camera to obtain a plurality of front images and a plurality of back images;

S902, combining the front image and the back image obtained by performing the image acquisition on the same leaf into a combined image, thus obtaining a plurality of combined images, correspondingly; and S903, generating a combined image processing instruction to indicate to sequentially input the plurality of combined images into the first anthracnose prediction model for processing.

As the image for training is the common image, the image used for official prediction should also be the combined image, correspondingly. As the combined image integrates front and back information of a leaf, the prediction result is more accurate.

Further, after the step S10 of inputting the to-be-analyzed citrus leaf image into the first anthracnose prediction model for processing to obtain a second prediction result output by the first anthracnose prediction model, and judging whether the second prediction result is that the to-be-analyzed citrus crop is infected by anthracnose, the method comprises:

S101, if the second prediction result is that the to-be-analyzed citrus crop is infected by anthracnose, retrieving a plurality of sensing data sequences for a designated area;

S102, calculating a similarity value between the plurality of sensing data sequences for the designated area and the plurality of to-be-analyzed sensing data sequences according to a preset similarity calculation method;

S103, judging whether the similarity value is greater than a preset similarity threshold or not; and S104, if the similarity value is greater than the preset similarity threshold, generating an early detection instruction to indicate to input the plurality of sensing data sequences for the designated area into the first anthracnose prediction model for processing after completing the detection of the to-be-analyzed sensing data sequences.

Therefore, the pre-analysis capacity of the scheme of the present application is further improved. If there are a plurality of similar areas, in a case that one of the areas is detected to have anthracnose (which is obtained by leaf image detection at the moment, thus the area is in the symptom appearance), other similar areas are likely to have anthracnose. Therefore, it is preferable to detect these similar areas. It needs to be noted that the citrus crops in these areas may not be in the symptom appearance but may be in other two stages, hence, after being processed in the first anthracnose prediction model, if determining that the citrus crop is not in the symptom appearance, the second anthracnose prediction model also needs to be used to judge whether the citrus crop is in the other two stages.

The method for detecting an infection stage of anthracnose pathogen with pre-analysis capacity comprises: obtaining a plurality of sample sensing data sequences; obtaining a sample citrus leaf image; obtaining a first prediction result output by a first anthracnose prediction model; if the first prediction result is that a sample citrus crop is not infected by anthracnose, obtaining sample Raman spectral data and sample hyperspectral data; obtaining a first judgment result, and obtaining a second judgment result; performing labeling on the plurality of sample sensing data sequences to label the first judgment result and the second judgment result, thus obtaining second training data; training a neural network model to obtain a second anthracnose prediction model; obtaining a plurality of to-be-analyzed sensing data sequences; obtaining a to-be-analyzed citrus leaf image; obtaining a second prediction result output by the first anthracnose prediction model; if the second prediction result is that a to-be-analyzed citrus crop is not infected by anthracnose, obtaining a third prediction result; if the third prediction result is that the leaf of the to-be-analyzed citrus crop is in the penetration period, generating a Raman spectral detection instruction; if the third prediction result is that the leaf of the to-be-analyzed citrus crop is in the incubation period, generating a hyperspectral detection instruction, thus completing the pre-analysis to the infection progress of the anthracnose pathogen, and achieving rapid detection before symptom appearance of anthracnose.

A means for detecting an infection stage of anthracnose pathogen with pre-analysis capacity is provided in an embodiment of the present application, comprising:

a sample sensing data sequence acquisition unit for indicating to perform data acquisition processing in a first time cycle using a plurality of sensors arranged at a sample area, thus obtaining a plurality of sample sensing data sequences, wherein the plurality of sample sensing data sequences at least comprise a temperature data sequence and a humidity data sequence, sample citrus crops are planted in the sample area, and the sample citrus crops have not been found to be infected by the anthracnose pathogen prior to the first time cycle;

a sample citrus leaf image acquisition unit for indicating to perform image acquisition processing on a leaf of the sample citrus crop using a preset camera to obtain a sample citrus leaf image;

a first prediction result judgment unit for indicating to input the sample citrus leaf image into the first anthracnose prediction model for processing to obtain a first prediction result output by the first anthracnose prediction model, and judging whether the first prediction result is that the sample citrus crop is infected by anthracnose, wherein the first anthracnose prediction model is obtained by training by taking a leaf image of a citrus crop in symptom appearance as first training data based on a deep convolutional neural network model; and the infection progress of the anthracnose pathogen to the citrus crop is totally divided into three stages: a penetration period, an incubation period, and symptom appearance;

a sample Raman spectral data acquisition unit for indicating to perform Raman spectral detection and hyperspectral detection processing on the leaf of the sample citrus crop respectively if the first prediction result is that the sample citrus crop is not infected by anthracnose, thus obtaining sample Raman spectral data and sample hyperspectral data;

a first judgment result acquisition unit for indicating to judge whether the leaf of the citrus crop is in the penetration period or not according to the sample Raman spectral data, thus obtaining a first judgment result, and indicating to judge whether the leaf of the sample citrus crop is in the incubation period or not according to the sample hyperspectral data, thus obtaining a second judgment result;

a second training data acquisition unit for indicating to perform labeling on the plurality of sample sensing data sequences to label the first judgment result and the second judgment result, thus obtaining second training data;

a second anthracnose prediction model acquisition unit for indicating to perform training on the preset neural network model using the second training data to obtain a second anthracnose prediction model;

a to-be-analyzed sensing data sequence acquisition unit for indicating to perform data acquisition processing in a second time cycle using a plurality of sensors arranged in a to-be-analyzed area, thus obtaining a plurality of to-be-analyzed sensing data sequences, wherein the types of the plurality of to-be-analyzed sensing data sequences are the same as the types of the plurality of sample sensing data sequences in a one-to-one correspondence manner, to-be-analyzed citrus crops are planted in the to-be-analyzed area, and the to-be-analyzed citrus crops have not been found to be infected by the anthracnose pathogen prior to the second time cycle;

a to-be-analyzed citrus leaf image acquisition unit for indicating to perform image acquisition processing on a leaf of a to-be-analyzed citrus crop using a preset camera to obtain a to-be-analyzed citrus leaf image;

a second prediction result judgment unit for indicating to input the to-be-analyzed citrus leaf image into the first anthracnose prediction module for processing to obtain a second prediction result output by the first anthracnose prediction model, and judging whether the second prediction result is that the to-be-analyzed citrus crop is infected by anthracnose;

a third prediction result acquisition unit for indicating to input the plurality of to-be-analyzed sensing data sequences into the second anthracnose prediction model for processing if the second prediction result is that the to-be-analyzed citrus crop is not infected by anthracnose, thus obtaining a third prediction result, wherein the third prediction result is that the leaf of the to-be-analyzed citrus crop is in the penetration period, in the incubation period or is not infected by the anthracnose pathogen;

a Raman spectral detection instruction generation unit for indicating to generate a Raman spectral detection instruction if the third prediction result is that the leaf of the to-be-analyzed citrus crop is in the penetration period, thus indicating to perform Raman spectral detection processing on the to-be-analyzed citrus crop; and a hyperspectral detection instruction generation unit for indicating to generate a hyperspectral detection instruction if the third detection result is that the leaf of the to-be-analyzed citrus crop is in the incubation period, thus indicating to perform hyperspectral detection processing on the to-be-analyzed citrus crop.

Wherein the operations respectively executed by the units are in one-to-one correspondence with the steps of the method for detecting the infection stage of the anthracnose pathogen with the pre-analysis capacity in the embodiment, and will not be described in detail here.

A means for detecting an infection stage of anthracnose pathogen with pre-analysis capacity provided by the present application comprises the following operations: obtaining a plurality of sample sensing data sequences; obtaining a sample citrus leaf image; obtaining a first prediction result output by a first anthracnose prediction model; if the first prediction result is that a sample citrus crop is not infected by anthracnose, obtaining sample Raman spectral data and sample hyperspectral data; obtaining a first judgment result, and obtaining a second judgment result; performing labeling on the plurality of sample sensing data sequences to label the first judgment result and the second judgment result, thus obtaining second training data; training a neural network model to obtain a second anthracnose prediction model; obtaining a plurality of to-be-analyzed sensing data sequences; obtaining a to-be-analyzed citrus leaf image; obtaining a second prediction result output by the first anthracnose prediction model; if the second prediction result is that a to-be-analyzed citrus crop is not infected by anthracnose, obtaining a third prediction result; if the third prediction result is that the leaf of the to-be-analyzed citrus crop is in the penetration period, generating a Raman spectral detection instruction; if the third prediction result is that the leaf of the to-be-analyzed citrus crop is in the incubation period, generating a hyperspectral detection instruction, thus completing the pre-analysis to the infection progress of the anthracnose pathogen, and achieving rapid detection before symptom appearance of anthracnose.

Figure 2:
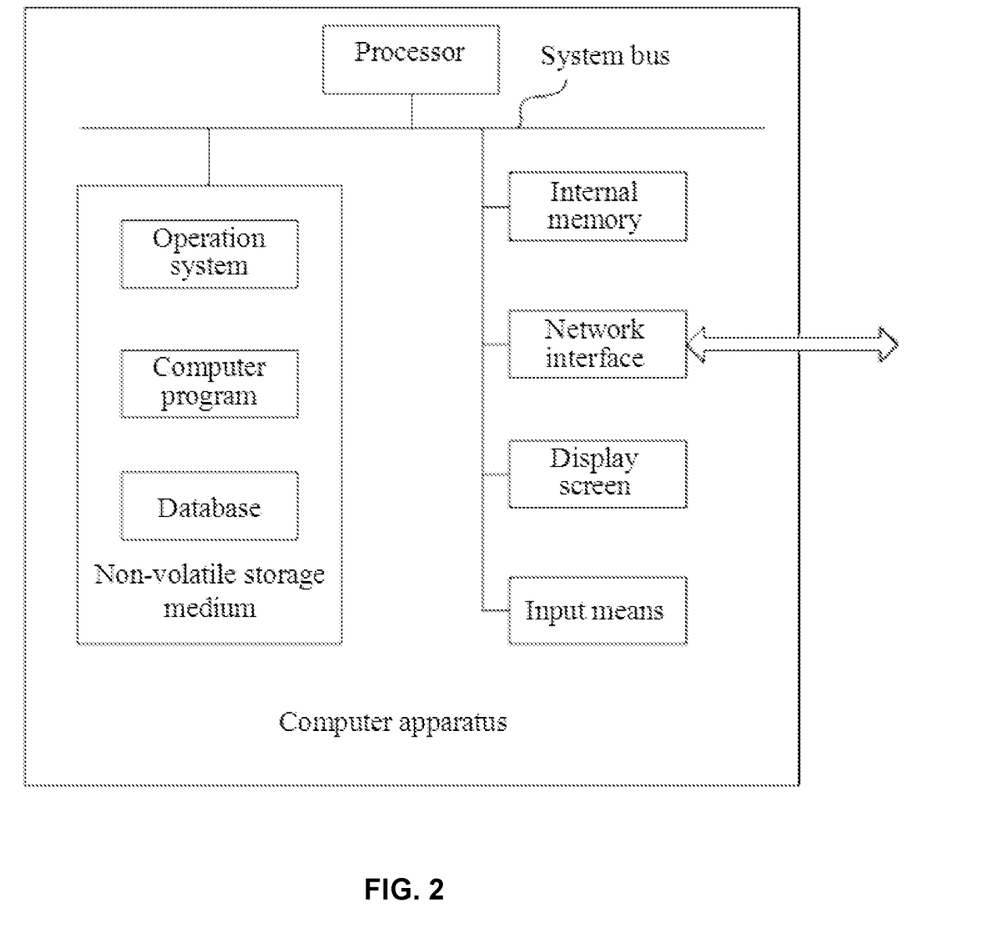
FIG. 2 is a structure schematic block diagram of a computer apparatus of one embodiment of the present application.

Referring to FIG. 2, a computer apparatus is further provided in the embodiment of the present invention, the computer apparatus nay be a server, an internal structure of which may be as shown in the figure. The computer apparatus comprises a processor, a memory, a network interface and a database which are connected by a system bus. Wherein the processor of the computer apparatus is used for providing capability of calculation and control. The memory of the computer apparatus comprises a non-volatile storage medium and an internal memory. The non-volatile storage medium stores an operation system, computer programs, and a database. The internal memory provides an environment for the operation of the operation system and the computer programs in the non-volatile storage medium. The database of the computer apparatus is used for storing the data used by a method for detecting an infection stage of anthracnose pathogen with pre-analysis capacity. The network interface of the computer apparatus is used for communicating with an external terminal through network connection. The computer programs, when executed by the processor, implement a method for detecting an infection stage of anthracnose pathogen with pre-analysis capacity. The computer apparatus further comprises a display screen and an input means which are respectively used for displaying a man-machine interaction interface and for receiving input data.

The processor executes the method for detecting the infection stage of the anthracnose pathogen with pre-analysis capacity, wherein the steps included by the method are in one-to-one correspondence with the steps of the method for detecting the infection stage of the anthracnose pathogen with the pre-analysis capacity in the embodiment, which will not be described in detail here.

It may be understood by those of ordinary skill in the art that the structures shown in the figures are merely block diagrams of partial structures associated with the scheme of the present application and do not constitute limitations of the computer apparatus to which the scheme of the present application is applied.

The computer apparatus provided by the present application comprises the following steps: obtaining a plurality of sample sensing data sequences; obtaining a sample citrus leaf image; obtaining a first prediction result output by a first anthracnose prediction model; if the first prediction result is that a sample citrus crop is not infected by anthracnose, obtaining sample Raman spectral data and sample hyperspectral data; obtaining a first judgment result, and obtaining a second judgment result; performing labeling on the plurality of sample sensing data sequences to label the first judgment result and the second judgment result, thus obtaining second training data; training a neural network model to obtain a second anthracnose prediction model; obtaining a plurality of to-be-analyzed sensing data sequences; obtaining a to-be-analyzed citrus leaf image; obtaining a second prediction result output by the first anthracnose prediction model; if the second prediction result is that a to-be-analyzed citrus crop is not infected by anthracnose, obtaining a third prediction result; if the third prediction result is that the leaf of the to-be-analyzed citrus crop is in the penetration period, generating a Raman spectral detection instruction; if the third prediction result is that the leaf of the to-be-analyzed citrus crop is in the incubation period, generating a hyperspectral detection instruction, thus completing the pre-analysis to the infection progress of the anthracnose pathogen, and achieving rapid detection before symptom appearance of anthracnose.

A computer readable storage medium having computer programs stored thereon is further provided by one embodiment of the present application. The computer programs, when executed by a processor, implement a method for detecting an infection stage of anthracnose pathogen with pre-analysis capacity, wherein the steps included by the method are in one-to-one correspondence with the steps of executing the method for detecting the infection stage of anthracnose pathogen with pre-analysis capacity of the foregoing embodiment, and will not be described in detail here.

It needs to be noted that the terms comprise, include or any other variation thereof herein are intended to cover non-exclusive inclusion, thus making a process, an apparatus, an object, or a method that comprises a series of elements includes not only those elements, but also other elements not expressly listed, or elements inherent in such process, apparatus, article, or method. An element defined by the statement "comprises a . . . " does not, without more constraints, exclude the existence of additional identical elements in the process, apparatus, article, or method that comprises the element.

The above is only a preferred embodiment of the present application and is not intended to limit the scope of patent for the present application. Equivalent structure or equivalent flow transformation made by utilizing the contents of the specification and drawings of the present application or direct or indirect application in other related technical fields are included in the scope of patent protection of the present application in a similar way.

The invention claimed is:

1. A method for detecting an infection stage of anthracnose pathogen with pre-analysis capacity, comprising:
   S1: performing data acquisition processing in a first time cycle using a plurality of sensors arranged in a sample area, thus obtaining a plurality of sample sensing data sequences, wherein the plurality of sample sensing data sequences at least comprise a temperature data sequence and a humidity data sequence, sample citrus crops are planted in the sample area, and the sample citrus crops have not been found to be infected by the anthracnose pathogen prior to the first time cycle;
   S2: performing image acquisition processing on a leaf of the sample citrus crop using a preset camera to obtain a sample citrus leaf image;
   S3: inputting the sample citrus leaf image into a preset first anthracnose prediction model for processing to obtain a first prediction result output by the first anthracnose prediction model, and judging whether the first prediction result is that the sample citrus crop is infected by anthracnose, wherein the first anthracnose prediction model is obtained by training by taking a leaf image of the citrus crop in symptom appearance as first training data based on a deep convolutional neural network model; and the infection progress of the anthracnose pathogen to the citrus crop is totally divided into three stages: a penetration period, an incubation period, and symptom appearance;
   S4: if the first prediction result is that the sample citrus crop is not infected by anthracnose, performing Raman spectral detection and hyperspectral detection on the leaf of the sample citrus crop respectively to obtain sample Raman spectral data and sample hyperspectral data;
   S5: judging whether the leaf of the sample citrus crop is in the penetration period or not according to the sample Raman spectral data, thus obtaining a first judgment result; and judging whether the leaf of the sample citrus crop is in the incubation period or not according to the sample hyperspectral data, thus obtaining a second judgment result;
   S6, performing labeling on the plurality of sample sensing data sequences to label the first judgment result and the second judgment result, thus obtaining second training data;
   S7, training a preset neural network model using the second training data to obtain a second anthracnose prediction model;
   S8, performing data acquisition processing in a second time cycle using a plurality of sensors arranged in a to-be-analyzed area, thus obtaining a plurality of to-be-analyzed sensing data sequences, wherein the types of the plurality of to-be-analyzed sensing data sequences are the same as the types of the plurality of sample sensing data sequences in a one-to-one correspondence manner, to-be-analyzed citrus crops are planted in the to-be-analyzed area, and the to-be-analyzed citrus crops have not been found to be infected by the anthracnose pathogen prior to the second time cycle;
   S9, performing image acquisition processing on a leaf of the to-be-analyzed citrus crop using a preset camera to obtain a to-be-analyzed citrus leaf image;
   S10, inputting the to-be-analyzed citrus leaf image into the first anthracnose prediction model for processing to obtain a second prediction result output by the first anthracnose prediction model, and judging whether the second prediction result is that the to-be-analyzed citrus crop is infected by anthracnose;
   S11, if the second prediction result is that the to-be-analyzed citrus crop is not infected by anthracnose, inputting the plurality of to-be-analyzed sensing data sequences into the second anthracnose prediction model for processing to obtain a third prediction result, wherein the third prediction result is that the leaf of the to-be-analyzed citrus crop is in the penetration period, in the incubation period, or is not infected by the anthracnose pathogen;
   S12, if the third prediction result is that the leaf of the to-be-analyzed citrus crop is in the penetration period, generating a Raman spectral detection instruction to indicate to perform Raman spectral detection processing on the to-be-analyzed citrus crop; and
   S13, if the third prediction result is that the leaf of the to-be-analyzed citrus crop is in the incubation period, generating a hyperspectral detection instruction to indicate to perform hyperspectral detection on the to-be-analyzed citrus crop.

2. The method for detecting the infection stage of the anthracnose pathogen with pre-analysis capacity according to claim 1, wherein prior to the step S3 of inputting the sample citrus leaf image into a preset first anthracnose prediction model for processing to obtain a first prediction result output by the first anthracnose prediction model and judging whether the first prediction result is that the sample citrus crop is infected by anthracnose, the method comprises:
   S21, retrieving a plurality of sample images from a preset database, wherein the sample images are images obtained by collecting leaves of a citrus crop in symptom appearance;

- S22, dividing the plurality of sample images into a plurality of training images and a plurality of verifying images according to a preset proportion;
- S23, retrieving a preset deep convolutional neural network model, and inputting the plurality of training images into the deep convolutional neural network model for training to obtain a temporary anthracnose prediction model;
- S24, performing verification processing on the temporary anthracnose prediction model using the plurality of verifying images, and judging whether a verification processing result is that the verification is passed; and
- S25, if the verification processing result is that the verification is passed, recording the temporary anthracnose prediction model as the first anthracnose prediction model.

3. The method for detecting the infection stage of the anthracnose pathogen with pre-analysis capacity according to claim 2, wherein the step S21 of retrieving a plurality of sample images from a preset database, wherein the sample images are images obtained by collecting leaves of the citrus crop in the symptom appearance, comprises:
- S211, performing image acquisition processing on the front and the back of one leaf of the citrus crop in the symptom appearance to obtain a front image and a back image; and
- S212, combining the front image and the back image corresponding to each other into a common image, and recording the common image as a sample image.

4. The method for detecting the infection stage of the anthracnose pathogen with pre-analysis capacity according to claim 3, wherein the step S9 of performing image acquisition processing on a leaf of the to-be-analyzed citrus crop using a preset camera to obtain a to-be-analyzed citrus leaf image comprises:
- S901, performing data acquisition processing on the fronts and the backs of a plurality of leaves of the to-be-analyzed citrus crop using the preset camera to obtain a plurality of front images and a plurality of back images;
- S902, combining the front image and the back image obtained by performing the image acquisition on the same leaf into a combined image, thus obtaining a plurality of combined images, correspondingly; and
- S903, generating a combined image processing instruction to indicate to sequentially input the plurality of combined images into the first anthracnose prediction model for processing.

5. The method for detecting the infection stage of the anthracnose pathogen with pre-analysis capacity according to claim 1, after the step S10 of inputting the to-be-analyzed citrus leaf image into the first anthracnose prediction model for processing to obtain a second prediction result output by the first anthracnose prediction model, and judging whether the second prediction result that the to-be-analyzed citrus crop is infected by anthracnose, the method further comprises:
- S101, if the second prediction result is that the to-be-analyzed citrus crop is infected by anthracnose, retrieving a plurality of sensing data sequences for a designated area;
- S102, calculating a similarity value between the plurality of sensing data sequences for the designated area and the plurality of to-be-analyzed sensing data sequences according to a preset similarity calculation method;
- S103, judging whether the similarity value is greater than a preset similarity threshold or not; and
- S104, if the similarity value is greater than the preset similarity threshold, generating an early detection instruction to indicate to input the plurality of sensing data sequences for the designated area into the first anthracnose prediction model for processing after completing the detection of the to-be-analyzed sensing data sequences.

6. A means for detecting an infection stage of anthracnose pathogen with pre-analysis capacity, comprising:
- a sample sensing data sequence acquisition unit for indicating to perform data acquisition processing in a first time cycle using a plurality of sensors arranged at a sample area, thus obtaining a plurality of sample sensing data sequences, wherein the plurality of sample sensing data sequences at least comprise a temperature data sequence and a humidity data sequence, sample citrus crops are planted in the sample area, and the sample citrus crops have not been found to be infected by the anthracnose pathogen prior to the first time cycle;
- a sample citrus leaf image acquisition unit for indicating to perform image acquisition processing on a leaf of the sample citrus crop using a preset camera to obtain a sample citrus leaf image;
- a first prediction result judgment unit for indicating to input the sample citrus leaf image into the first anthracnose prediction model for processing to obtain a first prediction result output by the first anthracnose prediction model, and judging whether the first prediction result is that the sample citrus crop is infected by anthracnose, wherein the first anthracnose prediction model is obtained by training by taking a leaf image of a citrus crop in symptom appearance as first training data based on a deep convolutional neural network model; and the infection progress of the anthracnose pathogen to the citrus crop is totally divided into three stages: a penetration period, an incubation period, and symptom appearance;
- a sample Raman spectral data acquisition unit for indicating to perform Raman spectral detection and hyperspectral detection processing on the leaf of the sample citrus crop respectively if the first prediction result is that the sample citrus crop is not infected by anthracnose, thus obtaining sample Raman spectral data and sample hyperspectral data;
- a first judgment result acquisition unit for indicating to judge whether the leaf of the citrus crop is in the penetration period or not according to the sample Raman spectral data, thus obtaining a first judgment result, and indicating to judge whether the leaf of the sample citrus crop is in the incubation period or not according to the sample hyperspectral data, thus obtaining a second judgment result;
- a second training data acquisition unit for indicating to perform labeling on the plurality of sample sensing data sequences to label the first judgment result and the second judgment result, thus obtaining second training data;
- a second anthracnose prediction model acquisition unit for indicating to perform training on the preset neural network model using the second training data to obtain a second anthracnose prediction model;
- a to-be-analyzed sensing data sequence acquisition unit for indicating to perform data acquisition processing in a second time cycle using a plurality of sensors arranged in a to-be-analyzed area, thus obtaining a plurality of to-be-analyzed sensing data sequences, wherein the types of the plurality of to-be-analyzed sensing data sequences are the same as the types of the plurality of sample sensing data sequences in a one-to-one correspondence manner, to-be-analyzed citrus crops are planted in the to-be-analyzed area, and the to-be-analyzed citrus crops have not been found to be infected by the anthracnose pathogen prior to the second time cycle;

a to-be-analyzed citrus leaf image acquisition unit for indicating to perform image acquisition processing on a leaf of a to-be-analyzed citrus crop using a preset camera to obtain a to-be-analyzed citrus leaf image;

a second prediction result judgment unit for indicating to input the to-be-analyzed citrus leaf image into the first anthracnose prediction module for processing to obtain a second prediction result output by the first anthracnose prediction model, and judging whether the second prediction result is that the to-be-analyzed citrus crop is infected by anthracnose;

a third prediction result acquisition unit for indicating to input the plurality of to-be-analyzed sensing data sequences into the second anthracnose prediction model for processing if the second prediction result is that the to-be-analyzed citrus crop is not infected by anthracnose, thus obtaining a third prediction result, wherein the third prediction result is that the leaf of the to-be-analyzed citrus crop is in the penetration period, in the incubation period or is not infected by the anthracnose pathogen;

a Raman spectral detection instruction generation unit for indicating to generate a Raman spectral detection instruction if the third prediction result is that the leaf of the to-be-analyzed citrus crop is in the penetration period, thus indicating to perform Raman spectral detection processing on the to-be-analyzed citrus crop; and a hyperspectral detection instruction generation unit for indicating to generate a hyperspectral detection instruction if the third detection result is that the leaf of the to-be-analyzed citrus crop is in the incubation period, thus indicating to perform hyperspectral detection processing on the to-be-analyzed citrus crop.

\* \* \* \* \*